US011680239B2

(12) United States Patent
Bransby et al.

(10) Patent No.: US 11,680,239 B2
(45) Date of Patent: Jun. 20, 2023

(54) FILTER FOR MAMMALIAN CELL CULTURE PERFUSION AND CLARIFICATION WITH HYDROPHOBIC HOLLOW FIBER

(71) Applicant: Repligen Corporation, Waltham, MA (US)

(72) Inventors: Michael Bransby, Altadena, CA (US); Derek Carroll, Los Angeles, CA (US); Philip Yuen, Long Beach, CA (US)

(73) Assignee: Repligen Corporation, Waltham, MA (US)

( * ) Notice: Subject to any disclaimer, the term of this patent is extended or adjusted under 35 U.S.C. 154(b) by 624 days.

(21) Appl. No.: 16/730,516

(22) Filed: Dec. 30, 2019

(65) Prior Publication Data

US 2020/0208092 A1 Jul. 2, 2020

Related U.S. Application Data

(60) Provisional application No. 62/846,934, filed on May 13, 2019, provisional application No. 62/786,884, filed on Dec. 31, 2018.

(51) Int. Cl.
 *C12M 1/12* (2006.01)
 *C12M 3/00* (2006.01)
 (Continued)

(52) U.S. Cl.
 CPC ............ *C12M 25/10* (2013.01); *B01D 63/04* (2013.01); *B01D 69/081* (2013.01); *B01D 71/26* (2013.01);
 (Continued)

(58) Field of Classification Search
None
See application file for complete search history.

(56) References Cited

U.S. PATENT DOCUMENTS 5,658,466 A   8/1997  Kawaguchi et al.
5,989,431 A   11/1999 Evans et al.
(Continued)

FOREIGN PATENT DOCUMENTS

CA    2951046 A1   12/2015
CN    102164657 A   8/2011
(Continued)

OTHER PUBLICATIONS

International Search Report and Written Opinion dated May 11, 2020 for PCT/US2019/68972 filed Dec. 30, 2019.
(Continued)

*Primary Examiner* — Jason M Greene
(74) *Attorney, Agent, or Firm* — KDW Firm PLLC

(57) ABSTRACT

This disclosure relates to the use of a hydrophobic hollow fiber filter for the filtration of cell cultures and other biological perfusions, due to its resistance to fouling, as well as the ability to filter solutions with a high solid content. A hydrophobic hollow fiber filter may be used within a filter housing in conjunction with a process vessel and a traditional separation system. When the system is used with alternating tangential flow or tangential flow filtration, the hydrophobic hollow fiber filter results in more effective filtration of the filtrate, leading to greater concentration of the retentate, even in solution containing high levels of solids.

40 Claims, 5 Drawing Sheets

(51) Int. Cl.
  *B01D 69/08* (2006.01)
  *B01D 63/04* (2006.01)
  *C12M 1/00* (2006.01)
  *B01D 71/26* (2006.01)

(52) U.S. Cl.
  CPC ............ *C12M 21/08* (2013.01); *C12M 29/10* (2013.01); *B01D 2239/0428* (2013.01); *B01D 2239/1216* (2013.01); *B01D 2239/1225* (2013.01)

(56) References Cited

U.S. PATENT DOCUMENTS

| | | | |
|---|---|---|---|
| 2012/0145626 A1 | 6/2012 | Luttropp et al. | |
| 2017/0173536 A1* | 6/2017 | Nagata | B01D 71/26 |
| 2018/0361325 A1* | 12/2018 | Hiraoka | B01D 63/04 |

FOREIGN PATENT DOCUMENTS

| | | |
|---|---|---|
| CN | 105473214 A | 4/2016 |
| JP | S60232208 A | 11/1985 |
| JP | H04117600 U | 10/1992 |
| JP | 2005110695 A | 4/2005 |
| JP | 2013226486 A | 11/2013 |
| JP | 2014117190 A | 6/2014 |
| JP | 2014520534 A | 8/2014 |
| TW | M557639 U | 4/2018 |
| WO | 9604067 A1 | 2/1996 |
| WO | 9853894 A1 | 12/1998 |
| WO | 0158501 A1 | 8/2001 |
| WO | 2010036760 A1 | 4/2010 |
| WO | 2013047775 A1 | 4/2013 |
| WO | 2014180573 A1 | 11/2014 |
| WO | 2017082990 A1 | 5/2017 |

OTHER PUBLICATIONS

Chang, S. et al., Unstable filtration behavior with submerged hollow fiber membranes. Journal of Membrane Science, Feb. 1, 2008, vol. 308, No. 1-2, pp. 107-114.

Chung et al., "Evaluation of liquid-phase microextraction conditions for determination of chlorophenols in environmental samples using gas chromatography-mass spectrometry without derivatization" Taianta 76 (2008) 154-160.

European Search Report and Written Opinion for the European Application No. EP19906656, dated Jan. 25, 2023, 8 pages.

* cited by examiner

FILTER FOR MAMMALIAN CELL CULTURE PERFUSION AND CLARIFICATION WITH HYDROPHOBIC HOLLOW FIBER

PRIORITY

This application claims the benefit of priority to, U.S. Patent Application No. 62/786,844, filed Dec. 31, 2018, entitled "Filter For Mammalian Cell Culture Perfusion And Clarification With Polypropylene Hollow Fiber," and claims the benefit of priority to, U.S. Patent Application No. 62/846,934, filed May 13, 2019, entitled "Filter For Mammalian Cell Culture Perfusion And Clarification With Polypropylene Hollow Fiber," which application is incorporated herein by reference in its entirety.

FIELD OF THE DISCLOSURE

Embodiments of this disclosure relate generally to process filtration systems, and more particularly to systems utilizing hydrophobic hollow fiber membranes.

BACKGROUND

Filtration is used to separate, clarify, modify, and/or concentrate a fluid solution, mixture, or suspension. It is often a necessary step in the production, processing, and analysis stages of drugs, diagnostics, and chemicals by the biotechnical, pharmaceutical, and medical industries. Filtration may be used to remove a desired compound from a solution, for example, or to remove byproducts, leaving behind a more concentrated medium. These processes can be modified as appropriate by the selection of a variety of filter materials, pore sizes, and/or other filter variables.

When producing a cell culture, it is often necessary to filter waste from the developing culture. Advancements in biological manufacturing processes now allow for the large scale production of cell cultures, enabling the production of recombinant proteins, virus-like particles (VLP), gene therapy particles, and vaccines, often using process vessel devices. Cell retention devices which remove metabolic waste products and refresh the culture with additional nutrients are widely available. Commonly, this retention is performed using the perfusion of a process vessel culture with hollow fiber membranes using tangential flow filtration or alternating tangential flow filtration.

Additionally, industry trends indicate that bioprocessing operations are being extended or even made continuous. Such operations may extend into days, weeks, or months of operation. Many typical components, such as filters, are unable to adequately perform for such lengths of time without fouling or otherwise needing maintenance or replacement.

Hollow fiber membranes are often used in cell culture perfusion and clarification, but their use in these applications may be complicated by the potential for fouling of the membranes with cell debris. Fouling, in turn, may cause membranes to retain, rather than pass, the intended product. Hollow fiber membranes are typically made of polyethersulfone (PES), polysulfone, cellulosic and other materials which enable the creation of pores within the membranes. These pores are typically between 0.2 µm and 0.65 µm. PES has traditionally been used in bioprocessing applications due to its anionic supercharged nature, which prevents the cell debris from attaching. However, there is an ongoing need for improved membranes which resist fouling and while allowing filtration of solutions with a high solid content.

Polypropylene (PP) is a hydrophobic material which has been commonly used in industrial filtration. It is known that certain molecules are less likely to adsorb to the PP membrane compared to a PES membrane due to polar interactions between the molecules and the PES membrane. Specifically, polyphenols, polysaccharides, and tannins were found to have a much lower level of adsorption to PP membranes than to PES membranes. While polypropylene (PP) has been used to make hollow fiber membranes, these membranes are typically not used in biotechnological perfusion due to their extreme hydrophobicity and the belief that they will contribute to the denaturation of peptide biologics.

SUMMARY

Polypropylene has been found here to be appropriate for the filtration of cell cultures and other biological perfusions, due to its resistance to fouling, as well as the ability to filter solutions with a high solid content. A PP hollow fiber filter (such as that made by Membrana) may be used within a filter housing in conjunction with a process vessel and a traditional separation system. When the system is used with alternating tangential flow or tangential flow filtration, the PP hollow fiber filter results in more effective filtration of the filtrate, leading to greater concentration of the retentate, even in solution containing high levels of solids. Without wishing to be bound by any theory, in some cases, fouling is reduced at least in part by means of a tubular pinch effect, which is achieved by selecting appropriate internal fiber diameters for filter fluxes during the filtration process. This PP hollow fiber filter may be used in, for example, N-1 perfusion.

In an aspect, this disclosure describes a pre-wetted, single-use hollow fiber filter for perfusion cell culture. The filter may be pre-wetted with an alcohol and may be stored in a buffered solution.

In an embodiment, the filter may comprise a filter housing comprising an inlet, a retentate outlet, a permeate outlet, at least one hydrophobic hollow fiber extending between the inlet and retentate outlet, thereby fluidly separating the permeate outlet from the retentate outlet and the inlet, and a potting material connecting the hydrophobic hollow fibers to the filter housing and sealing at least one of the inlet and the retentate outlet from the permeate outlet.

In some embodiments, the hydrophobic hollow fiber may comprise a plurality of pores. The pores may be 0.05 µm to 2.0 µm in diameter. The hydrophobic hollow fiber may have a surface area of 10 $cm^2$ to 90 $m^2$. The hydrophobic hollow fiber may have an inner diameter of 0.2 mm to 5.0 mm. The hydrophobic hollow fiber may have a wall thickness of 50 µm to 500 µm. The hydrophobic hollow fiber may comprise a polyolefin or a fluoropolymer. The polyolefin may be polypropylene, polyethylene, or co-polymers thereof.

In an aspect, this disclosure describes a method for perfusion cell culture. This method may comprise circulating a cell culture fluid through the hydrophobic hollow fiber filter, thereby separating the cell culture fluid into a filtrate and a retentate, and returning the retentate to the bioreactor.

In some embodiments, the perfusion cell culture may be selected from the group consisting of: n-1 culture and media exchange, in either case wherein the filtrate is not retained. The perfusion cell culture may be selected from a group consisting of: high productivity harvest, concentrated fed batch culture, or continuous perfusion, in each case wherein the filtrate comprises a bioproduct of interest and is retained. The cell culture may be a mammalian cell culture, yeast cell culture, prokaryotic cell culture, or insect cell culture. The circulation of the cell culture may be performed by alternating tangential flow. The circulation of the cell culture may be performed by tangential flow filtration. The circulation of the cell culture fluid may be performed at a filter flux of 1, 2, 3, 4, 5, 10, 15, 20, 22.5, 25, 30 l/m²·h. The separation system may contain one or more of the following: peristaltic tubing through a peristaltic pumphead, maglev pump, ATF pump, and other positive displacement disposable pumps. The method may be performed over 10, 20, 30, 40, 50 days. The hydrophobic hollow fiber may comprise a polyolefin or a fluoropolymer. The polyolefin may be polypropylene, polyethylene, or co-polymers thereof.

In an aspect, this disclosure describes a method of assembling a perfusion culture system. This method may comprise disposing a pre-wetted hydrophobic hollow-fiber filter into a filter housing of the perfusion culture system and, optionally, connecting a permeate outlet of the filter housing to a permeate collection vessel, wherein: (a) the perfusion culture system comprises a process vessel, a first conduit fluidly connecting an interior of the process vessel to an interior of the filter housing to define a filter feed channel and, optionally, a second conduit connecting the interior of the filter housing to the process vessel and defining a retentate channel, and (b) prior to disposal within the filter housing the hydrophobic hollow fiber filter is pre-wetted with a solution comprising an alcohol and is stored in a buffered aqueous solution.

In some embodiments, the filter housing further may comprise an outlet for a filtrated, the outlet being fluidly separated from the feed and retentate channels by the hollow-fiber hydrophobic filter. The circulation of the cell culture fluid may be performed at a filter flux of 1, 2, 3, 4, 5, 10, 15, 20, 22.5, 25, 30 l/m²·h. The hydrophobic hollow fiber may comprise a polyolefin or a fluoropolymer. The polyolefin may be polypropylene, polyethylene, or co-polymers thereof.

In an aspect, this disclosure describes a method of perfusion cell culture. This method may comprise passing a cell culture medium tangentially across a hydrophobic filter to reduce a concentration of a first component of the cell culture medium, wherein the first component does not comprise a recombinant peptide, nucleic acid or viral capsid.

In some embodiments, the method may be performed over 10, 20, 30, 40, 50 days. The circulation of the cell culture fluid may be performed at a filter flux of 1, 2, 3, 4, 5, 10, 15, 20, 22.5, 25, 30 l/m²·h. The hydrophobic hollow fiber may comprise a polyolefin or a fluoropolymer. The polyolefin may be polypropylene, polyethylene, or co-polymers thereof.

In an aspect, the disclosure describes a method of filtering a fluid. This method may comprise passing the fluid through a hydrophobic hollow fiber filter system such that the fluid flows in a non-laminar manner through the hydrophobic hollow fiber filter, and such that the fluid is separated into a retentate and a permeate.

In an embodiment, a product of a feed velocity of the system and an inner diameter of the hydrophobic hollow fiber filter may be greater than 2500 mm²s⁻¹. A Reynolds number characterizing the flow of fluid into the filter may be greater than 2000, 2300, 2500, 3000, 3500, or 4000. The hydrophobic hollow fiber may comprise a polyolefin or a fluoropolymer. The polyolefin may be polypropylene, polyethylene, or co-polymers thereof.

In an aspect, this disclosure describes a method of filtering a fluid. This method may comprise passing the fluid through a hollow fiber filter under conditions in which a feed velocity is 2000, 2300, 2500, 3000, 3500 or 4000 times greater than the quotient of a kinematic viscosity of the fluid over the hollow fiber filter diameter.

In an embodiment, a direction of flow through the hydrophobic hollow fiber filter may be alternated. The method may further comprise a step of collecting a filter permeate. The hydrophobic hollow fiber filter may retain a non-desired species. The retained non-desired species may be selected from the group consisting of: a species of mammalian cell origin; a species of microbial cell origin; a species of viral origin; a protein; a nucleic acid; a polysaccharide; or a complex of any of the foregoing. A desired species may pass through the hydrophobic hollow fiber filter into a permeate. The desired species may be selected from the group consisting of: a species of mammalian cell origin; a species of microbial cell origin; a species of viral origin; a protein; a nucleic acid; a polysaccharide; a virus; a microcarrier; a particle; or a complex of any of the foregoing. A composition may comprise a permeate collected according to a method described in this disclosure. A concentration of a desired species in the composition may be at least 10×, 20×, 40×, 50×, 75× or 100× greater than a concentration of the desired species in the fluid. A concentration of non-desired species may be at least 10×, 20×, 40×, 50×, 75× or 100× less than a concentration of the non-desired species in the fluid. The method may further comprise the step of removing a permeate from the fluid, thereby increasing a concentration of a desired species that is retained by the hydrophobic hollow fiber filter, wherein the concentration of the desired species is increased by 5×, 10×, 20×, 40×, 50×, 75× or 100×. The desired species may be selected from the group consisting of: a species of mammalian cell origin; a species of microbial cell origin; a species of viral origin; a protein; a nucleic acid; a polysaccharide; a virus; a microcarrier; a particle; or a complex of any of the foregoing.

DETAILED DESCRIPTION

Overview

Figure 1A:
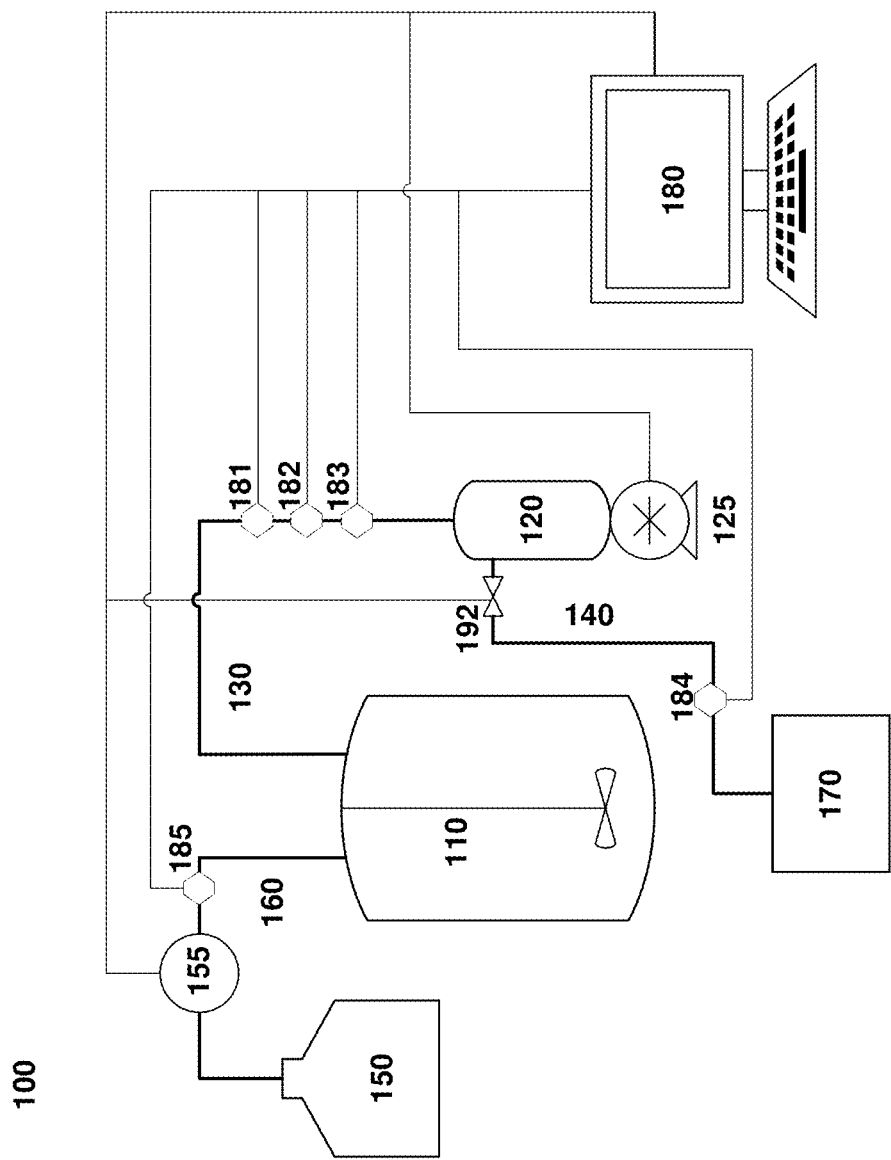
FIG. 1A. An exemplary system for clarification of cell cultures used in various embodiments of this disclosure.

Without wishing to be bound by any theory, the filtration process achieved in hydrophobic hollow fiber filter systems differs from filtering processes occurring in conventionally used PES hollow-fiber tangential flow filtration membranes, where intermediate-size particles may accumulate at the inner surface of the wall, resulting in the formation of a gel layer or filter cake and fouling of the filter.

The following disclosure focuses on hydrophobic hollow fiber filters which may include, without limitation, polyolefins such as polypropylene and polyethylene. The following disclosure focuses on polypropylene, however one of skill in the art will recognize that any similar polyolefin may be used unless otherwise indicated.

Polypropylene (PP) has been found here to be appropriate for the filtration of cell cultures and other biological perfusions, due to its resistance to fouling, as well as the ability to filter solutions with a high solid content. These performance characteristics may be advantageous for a number of bioprocessing applications; the present disclosure focuses on continuous perfusion cell culture and tangential flow filtration. In exemplary systems designed for these applications, a tangential-flow PP hollow fiber filter element is disposed within a filter housing to define feed/retentate and permeate (also referred to as filtrate) fluid channels separated from one another by the filter element. The feed/retentate fluid channel, in turn, is in fluid communication with a bioreactor or other process vessel, by means of a fluid coupling between the process vessel and an inlet (corresponding to a fluid feed) of the filter housing and, optionally, a return coupling between an outlet of the filter housing (corresponding to a retentate) and the process vessel. Perfusion culture systems according to this disclosure which utilize PP hollow fiber filter elements may offer more effective filtration of the filtrate with reduced fouling, leading to greater concentration of the retentate, even in solution containing high levels of solids.

Hollow fiber filter systems are characterized by several filter parameters and operating variables. Filter parameters include hollow fiber inner diameter (d), hollow fiber length (l), hollow fiber cross-sectional area (A) and number of hollow fiber units in the filter (N). Operating variables include feed flow rate ($Q_F$), kinematic viscosity ($\mu$), feed velocity per hollow fiber ($V_F$), shear rate ($\gamma$) and Reynolds number (Re). Relations between filter parameters and operating variables are set forth in Table 1:

TABLE 1

Filter parameters and operating variable relations

| | | |
|---|---|---|
| Hollow fiber cross-sectional area (A) | $\frac{\pi \cdot d^2}{4}$ | [1] |
| Feed velocity per hollow fiber ($V_F$) | $V_F = \frac{Q_F}{A \cdot N}$ | [2] |
| Shear rate ($\gamma$) | $\gamma = \frac{8 \cdot V_F}{d}$ | [3] |
| Reynolds number (Re) | $Re = \frac{V_F \cdot d}{\mu} = \frac{\gamma \cdot d^2}{8\mu}$ | [4] |

The Reynolds number is predictive of fluid flow behavior. When applied to fluid flows in tubular systems, laminar flows are expected where Reynolds numbers are below approximately 2300, turbulent are expected at Reynolds numbers above 4000, and a laminar-to-turbulent transition occurs between these values. While noting that laminar and turbulent flow behavior in hollow fiber filters may differ somewhat from the modeled behavior of non-permeable tubular systems, the inventors have found that hollow fiber filter systems according to this disclosure tolerate very high fluxes without fouling when the Reynolds number for the feed flow 150 is above the laminar flow range, e.g., above approximately 2300, 2500, 3000, 3500, 4000, etc. While not wishing to be bound by any theory, it is believed that turbulent feed flows may generate enhanced particle transport from the wall of hollow fiber filters to the bulk flow through the hollow fiber filters, which may reduce fouling compared to laminar flows. Accordingly, various embodiments of this disclosure are directed to methods of operating hollow fiber filter systems which utilize feed flows that are turbulent or within the laminar-to-turbulent transition region, e.g., characterized by Re values above 2000, 2300, 2500, 3000, 3500, 4000, etc. Because Re increases with increases in feed velocity, shear rate and/or hollow fiber filter inner diameter, certain methods of this disclosure involve operating a hollow fiber filter system with feed velocities or shear rates selected to yield Re values above 2000, 2300, 2500, 3000, 3500, 4000, etc. Because dilute aqueous solutions have a kinematic viscosity of approximately 1 centistoke (cSt), certain embodiments of the method involve operating a hollow fiber filter system under conditions in which a product of the feed velocity and the hollow fiber filter diameter is greater than 2000, 2300, 2500, 3000, 3500, or 4000 mm$^2$s$^{-1}$. In other embodiments, the method involves operating a hollow fiber filter system under conditions in which the feed velocity is 2000, 2300, 2500, 3000, 3500 or 4000 times greater than the quotient of the kinematic viscosity over the hollow fiber inner diameter ($\mu$d), which is approximately equal to 1/d for dilute aqueous solutions.

Additional embodiments of the disclosure are directed to hollow fiber filter systems configured for operation under conditions in which Re values exceed 2000, 2300, 2500, 3000, 3500, 4000, etc. In certain embodiments, a product of the feed velocity and the hollow fiber filter diameter is greater than 2000, 2300, 2500, 3000, 3500, or 4000 mm$^2$s$^{-1}$. Other embodiments of the disclosure relate to systems configured to operate under conditions in which the feed velocity is 2000, 2300, 2500, 3000, 3500 or 4000 times greater than the quotient of the kinematic viscosity over the hollow fiber filter inner diameter.

Certain embodiments of this disclosure utilize hollow fiber filter geometries that are selected to promote non-laminar flow. Increases in internal diameter, for example, will tend to promote more turbulent flows at the given shear rate. The hollow fiber filters used in the embodiments of the disclosure may have inner diameters greater than 1 mm and/or walls with a thickness greater than 0.1 mm to withstand operation under high-flux conditions. Systems and methods of this disclosure may be employed in alternating tangential flow (ATF) setups, or under a constant tangential flow, and any suitable pump technology may be employed to drive feed flows. The hollow fiber filter walls may have a constant or variable density and, consequently, a constant or variable average and maximum pore diameter across their length and/or circumference. The porosity of the hollow fiber filters may be further controlled by applying a coating or coatings to hollow fiber filter wall surfaces. Skilled artisans will appreciate that additional modifications of hollow fiber filter surfaces may be possible, including without limitation the use of affinity reagents to selectively purify specific molecular species (e.g., protein A coatings may be used to pull down human IgG).

Those of skill in the art will appreciate that, for feed flows characterized by Reynolds number at or just above the transition value of about 2300, decreases in velocity over the length of the hollow fiber filters may result in flows below the 2300 Re transition value within the hollow fiber filters. The inventors have found that improvements in filter capacity and fouling behavior are observed at Re values at the feed as low as 2300, indicating that a turbulent flow does not necessarily need to be maintained throughout the length of the hollow fiber filters, and that a turbulent flow across a portion of the length of the hollow fiber filters may be sufficient to improve filter capacity and fouling behavior to some degree. Thus, in certain embodiments of the disclosure, a hollow fiber filter system is operated under conditions in which VF at the feed is between 2300 and 2500, or between 2300 and 3000. In some embodiments, a hollow fiber filter system is operated such that a turbulent flow is produced across a portion of the length of the hollow fiber units in the filter.

Hollow fiber filter systems according to the present disclosure may be used to filter a variety of fluids and separate a variety of soluble or particulate species. These include, without limitation, mammalian cells or other eukaryotic cells, microbial cells, including bacterial cells such as *E. coli*, and/or synthetic nanoparticles, such as particles for drug delivery, as well as biomolecules such as polypeptides, polynucleotides, polysaccharides, and complexes of one or more of these. Without limiting the foregoing, the systems and methods of this disclosure can be used in the production and purification of recombinant proteins such as immunoglobins or functional fragments thereof. Those of skill in the art will appreciate that the systems and methods of this disclosure may be applied in any setting in which hollow-fiber TFF systems are currently used, such as clarifying animal or microbial cultures, concentration and fractionation of species such as those described above.

Hollow fibers for use in the present disclosure may have a wide range of lengths. In some embodiments, the hollow fibers may have a length ranging, for example, from 200 mm to 2000 mm in length, among other values. Hollow fibers such as those described above may be used to construct tangential flow filters for bioprocessing and pharmaceutical applications. Examples of bioprocessing applications in which such tangential flow filters may be employed include those where cell culture fluid is processed to separating cells from smaller particles such as proteins, viruses, virus like particles (VLPs), exosomes, lipids, DNA and other metabolites.

Such applications include perfusion applications in which smaller particles are continuously removed from cell culture medium as a permeate fluid while cells are retained in a retentate fluid returned to a bioreactor (and in which equivalent volumes of media are typically simultaneously added to the bioreactor to maintain overall reactor volume). Such applications further include clarification or harvest applications in which smaller particles (typically biological products) are more rapidly removed from cell culture medium as a permeate fluid.

Hollow fibers such as those described above may be used to construct hollow fiber filters for particle fractionation, concentration and washing. Examples of applications in which such hollow fiber filters may be employed include the removal of small particles from larger particles using such hollow fiber filters, the concentration of microparticles using such hollow fiber filters and washing microparticles using such hollow fiber filters.

Perfusion systems according to the present disclosure may comprise filter housings, conduits and other elements that are durable and can be sterilized (e.g., through autoclaving, steam cleaning, gamma irradiation, chemical sterilization, etc.); alternatively, one or more elements may be single-use and may be disposed of following use. One system component that may be advantageously designed for single use is the PP hollow fiber filter element itself. In some cases, moreover, the PP hollow fiber filter element may be provided as a sterilized, pre-wetted component: because of their hydrophobicity, these filter elements are generally wetted using non-polar or weakly polar solvents, such as alcohols (e.g., methanol, ethanol, glycol, etc.) and must be rinsed and equilibrated prior to use. In some instances, the PP hollow fiber filter is provided to an end user stored in a buffered solution such as deionized water or PBS. Further, it may be pre-wetted with an alcohol prior to use. In one aspect of this disclosure, the PP filter may be wet out with alcohol at the customer site. In yet another aspect, the PP filter may be hydrophilized with glycerin. In yet another aspect, the PP filter may be wet out during manufacturing and shipped wet with deionized water or PBS buffer.

The perfusion systems of this disclosure may comprise a reusable PP hollow fiber filter system. A reusable system may contain elements that may be sterilized (e.g., through autoclaving, steam cleaning, gamma irradiation, chemical sterilization, etc.). These reusable systems may further contain aseptic connections to a process vessel.

Perfusion systems according to the present disclosure may comprise: a hollow fiber filter comprising a PP membrane, a filter housing, a potting material, and one or more conduits with which the filter may be linked to a process vessel; and a process vessel. The process vessel of this disclosure may be a bioreactor. The PP membrane of this disclosure may include a plurality of pores which may be used to filter an intended product from a solution. Depending on the requirements of the particular application, the pore size can be in the range of 0.05 µm to 0.2 µm. The PP membrane may consist of hollow fibers and these hollow fibers may have an inner diameter of 0.2 mm to 5.0 mm. Further, the wall thickness of these hollow fibers may range from 50 to 500 µm. The hollow fibers may be arranged side by side (i.e. bundled) to form a hollow fiber filter. This bundling may lead to a surface area of 10 $cm^2$ to 90 $m^2$.

Fluid flows from the process vessel into the hollow fiber filter housing are typically driven by a pump, e.g., a mag-lev, peristaltic or diaphragm/piston pump, which may impel fluid in a single direction or may cyclically alternate the direction of flow.

In exemplary systems designed for these applications, a tangential-flow PP hollow fiber filter element is disposed within a filter housing to define feed/retentate and permeate fluid channels separated from one another by the filter element. These embodiments differ from existing systems in their use of PP membranes, a material previously not believed useful for this purpose. The embodiments described herein are advantageous in that the filters are extremely hydrophobic, an aspect previously thought to hinder the filtration process. However, this aspect has been found to allow more effective filtration of biological solutions with less fouling than other materials.

This disclosure further relates to a system for the filtration of biological solutions, comprising a hollow fiber filter and a process vessel. The hollow fiber filter includes a PP membrane. In various embodiments, the PP hollow fiber filter may be connected to a process vessel. In these embodiments, the filter may be used in either tangential flow filtration or alternating tangential flow filtration. When the system is used in tangential flow, the cells or other biological components may flow through the lumen of the fibers back to the reactor. When the system is used in alternating tangential flow, the cells or other biological components may be pumped back and forth in different directions across the membrane, directing flow of filtrate through the lumens and limiting fouling of the filter. The embodiments described herein are advantageous in that the PP membrane comprising the hollow fiber filter is hydrophobic, which in turn may allow for more effective flow through the membranes, as it allows for flow through the pores by filtrate, but may not allow for fouling conditions, due to the hydrophobic nature of the membranes.

This disclosure also describes a method of use for a system to filter biological solutions using a PP hollow fiber filter. In a group of embodiments, a PP hollow fiber filter may be placed into a filter housing. The filter housing may be connected to a process vessel through a first conduit and a filtrate vessel through a second conduit. A pump may be attached to the filter housing, opposite the first conduit to the process vessel. Activation of the pump may pull liquid through the PP hollow fiber filter. The solution which moves through the filter is the filtrate, and may be removed from the system. The solution which does not traverse the membrane is the retentate, and may be forced back into the process vessel. In some embodiments, the liquid is a biological liquid. In yet another embodiment, the liquid contains cells. In some instances, the retentate is pushed back through the filter to return to the process vessel.

Figure 1B:
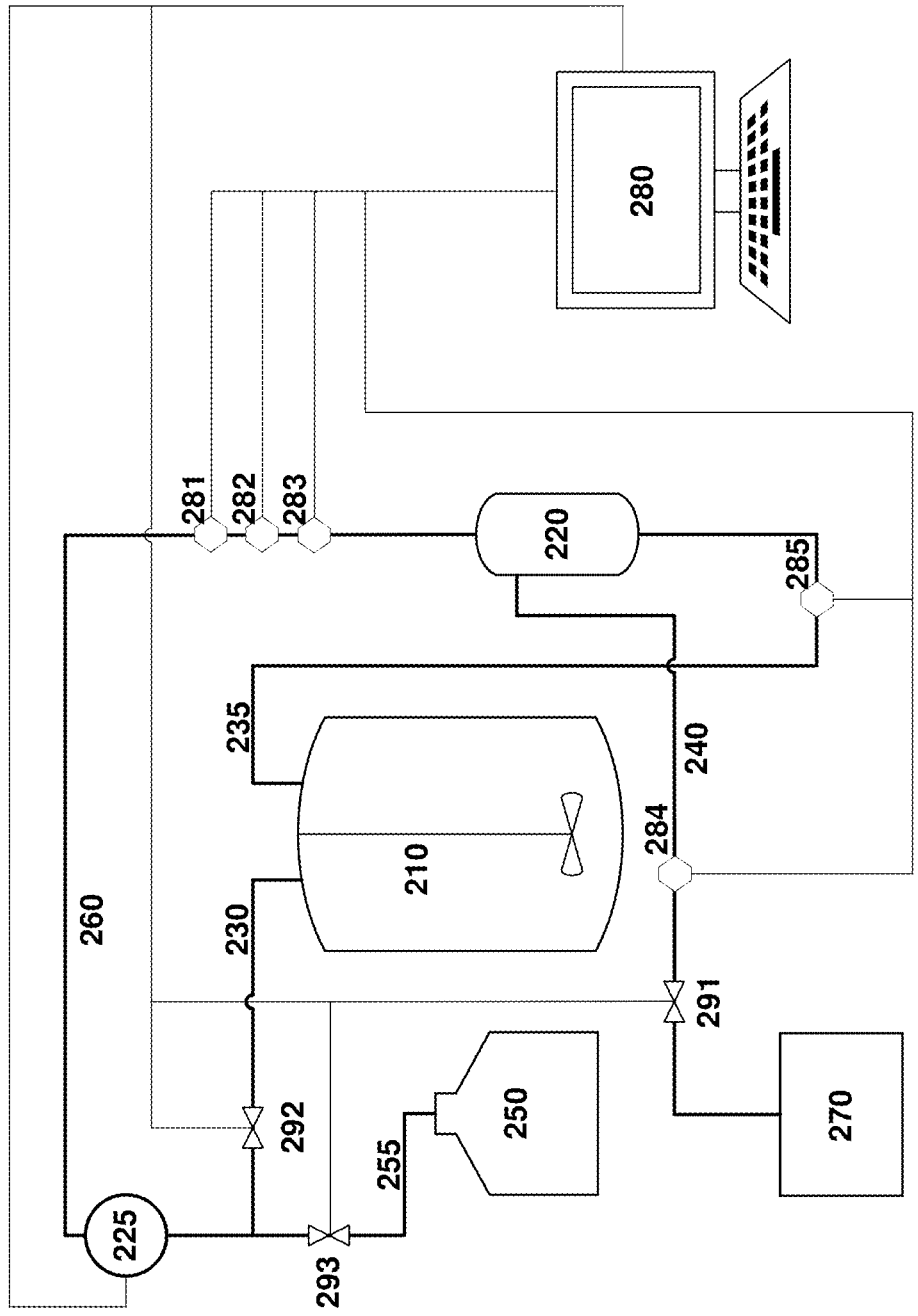
FIG. 1B. An exemplary system for clarification of cell cultures used in various embodiments of this disclosure.

FIGS. 1A and 1B depict exemplary perfusion culture systems according to the embodiments of this disclosure. The perfusion culture system 100 depicted in FIG. 1A is configured to provide alternating tangential flow filtration and, optionally, diafiltration. System 100 includes a process vessel 110, such as a bioreactor, and a filter unit 120, which comprises a filter (not shown) that separates the filter unit into two fluid compartments: a feed/retentate channel 130 and a permeate channel 140 (also referred to filtrate channel). The filter unit 120 is coupled to a positive displacement pump such as a piston or a diaphragm pump. The feed/retentate channel 130 runs between the process vessel 110 and the filter unit 120, while the permeate channel 140 runs to a permeate vessel 170. The system 100 also includes a diafiltration fluid vessel 150. Outflows from the diafiltration fluid vessel 150 pass through a flow control 155 (depicted here as a pump, but which may be a valve or other suitable device), into a diafiltration fluid channel 160 that connects the diafiltration fluid vessel 150 with the process vessel 110.

The system also includes a controller 180, depicted here as a general-purpose computer, but which may be any suitable device that can receive input, send output and perform operations automatically based on pre-programmed instructions. Controller 180 may receive user input through a peripheral device such as a keyboard, touchscreen, etc., and receives process data inputs from one or more sensors 181-183, which measure one or more variables in the culture within one or both of the process vessel 110 and the feed/retentate channel 130. (Though in the figure, the sensors 181-183 are depicted as connected to the feed/retentate channel 130 only). The controller also optionally receives input from one or more sensors 184, 185 in the permeate channel 140 and the diafiltration fluid channel 160, respectively. Variables measured by these sensors can include, without limitation, pressure, flow, pH, temperature, turbidity, optical density, impedance, or other variables relevant to the control of the clarification process.

Based on these inputs, and through execution of a pre-programmed control algorithm or heuristic that implements a control method described in greater detail below, the controller 180 generates one or more outputs, and sends data to components of the system 100 that regulate fluid flows, including the positive displacement pump 125, the diafiltration fluid control 155, and a permeate valve 192 regulating flows through the permeate channel 140.

Turning next to FIG. 1B, an alternative system design utilizes tangential flow filtration and constant-volume diafiltration. System 200 includes a process vessel 210 and a filtration unit 220, but which includes separate outflow 230 and return (retentate) 235 channels, such that the direction of flow through the filtration unit 220 remains constant during operation of the system, rather than alternating as in the system depicted in FIG. 1A. The outflow channel 230 merges with a diafiltration channel 255 from a diafiltration fluid vessel 250 into a single feed channel 260 of the filtration unit 220. The permeate channel 240, permeate vessel 270, controller 280, and sensors 281-285 are substantially as described above for the system depicted in FIG. 1A. Importantly, however, the constant-volume diafiltration process involves the control of multiple fluid channels, and so the controller 280 will send outputs to multiple valves 291, 292, 293, which regulate flows through the permeate channel 240, the process vessel output 230, and the diafiltration fluid output 255, respectively.

It should be noted that certain of the features of the perfusion culture systems described above can be modified without modification of other aspects of the system. For instance, although FIG. 1B depicts a TFF system configured for constant-volume diafiltration, those of skill in the art will appreciate that TFF systems may be used which do not provide constant-volume diafiltration, and that ATF systems can be used which do.

Figure 2A:
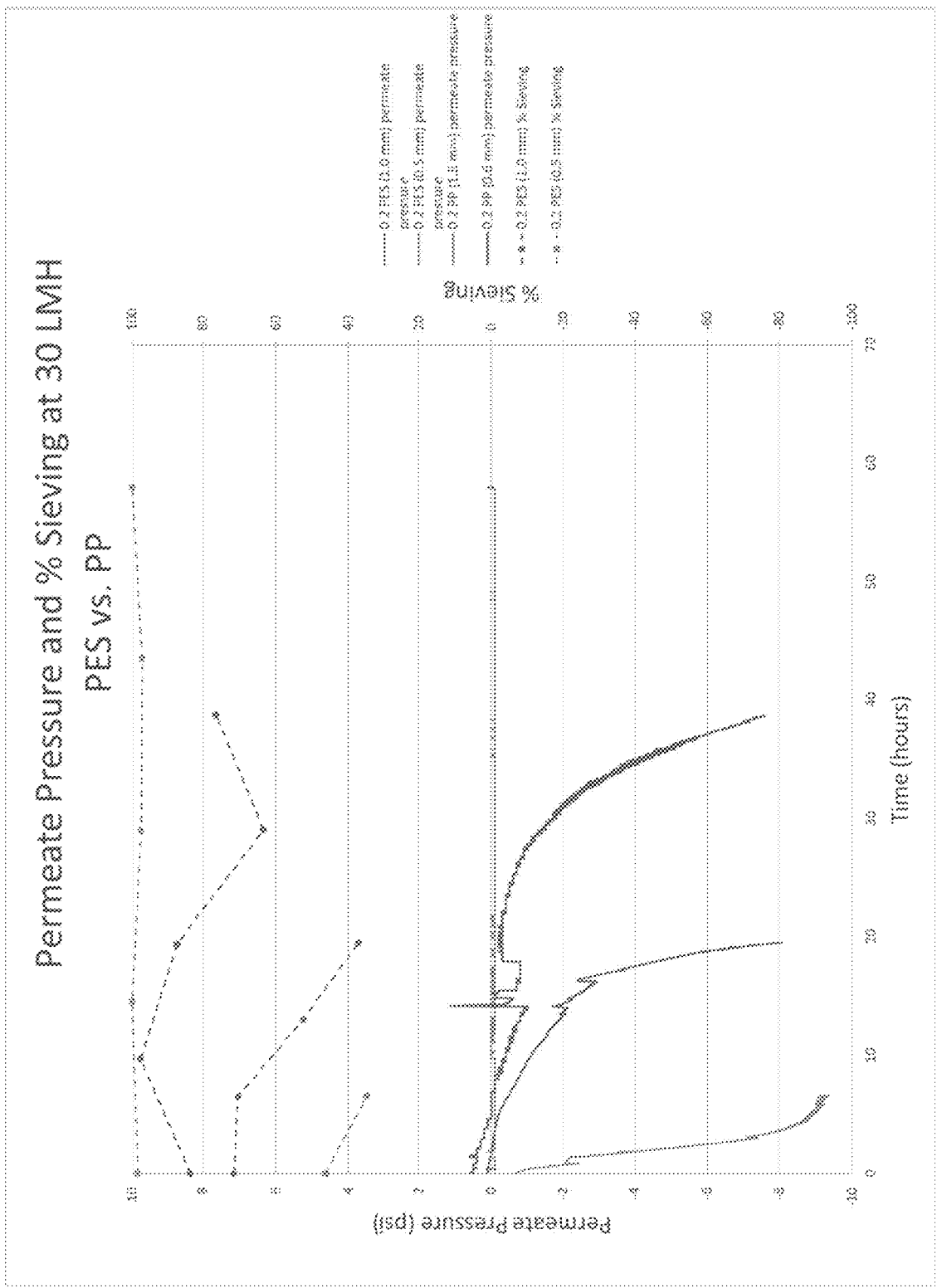
FIGS. 2A and 2B. Data showing the clarification of IgG antibodies performed under tangential flow (TF) mode using various filters.
Figure 2B:
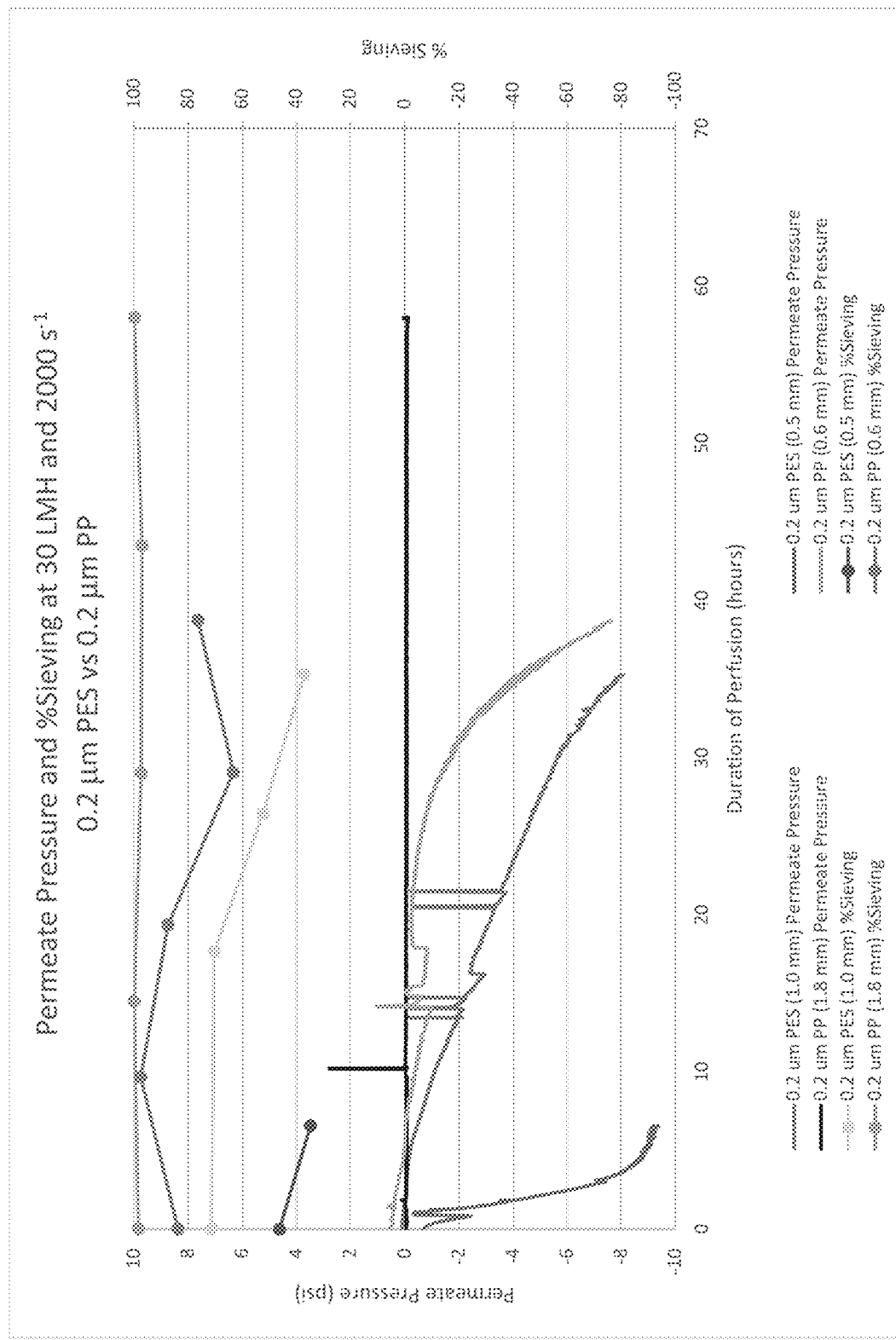

FIGS. 2A and 2B depict, for two separate experiments, the permeate pressure and percent sieving over time at 30 LMH of PES and PP hollow fiber filters.

Figure 3:
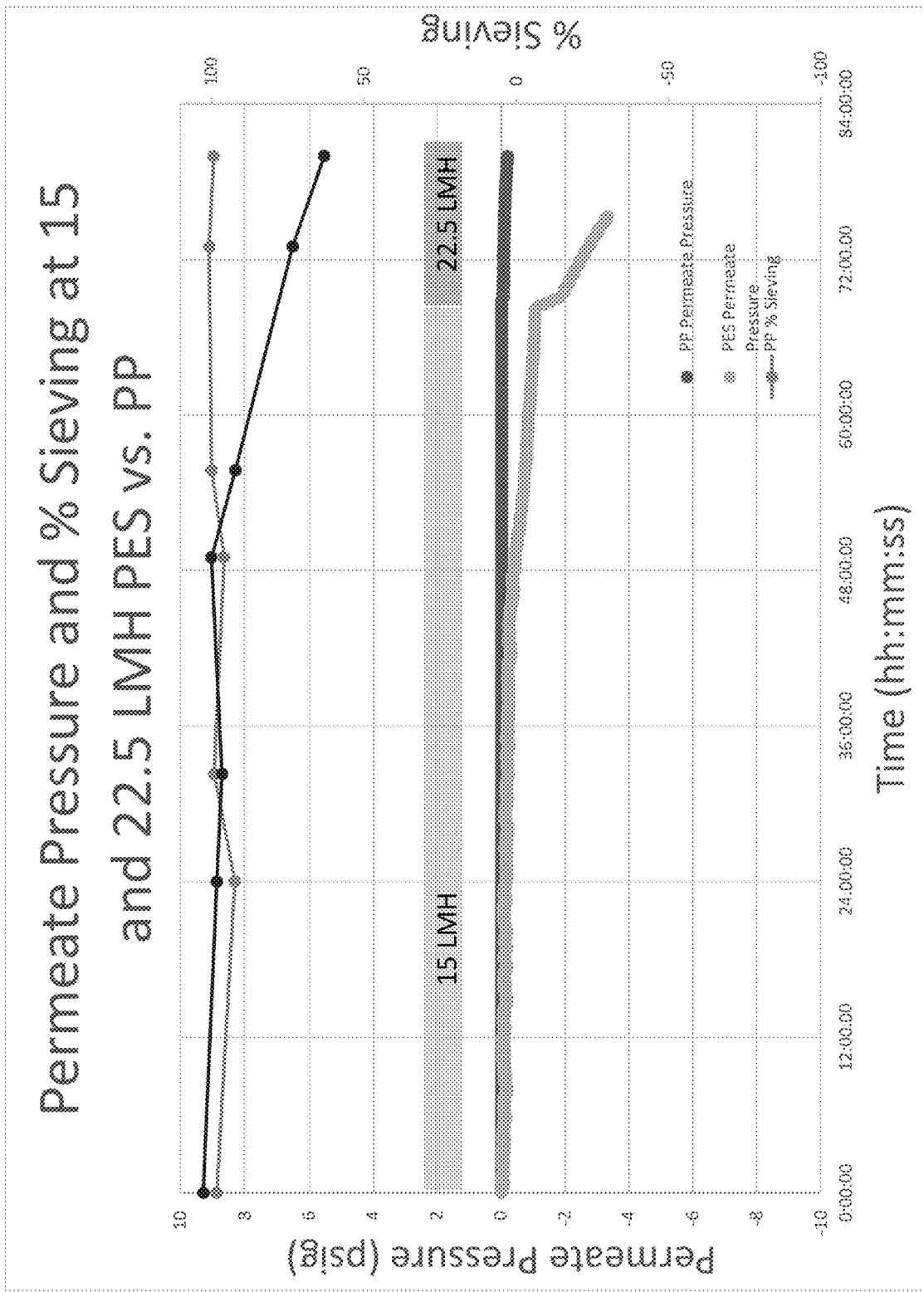
FIG. 3. Data showing the clarification of IgG antibodies performed under TF using polypropylene and PES filters at 15 and 22.5 LMH.

FIG. 3 depicts permeate pressure and percent sieving over time as described for FIGS. 2A and 2B above, but at a permeate flux of 15 LMH and 22.5 LMH. This figure shows the difference in fouling between the PES and PP hollow fiber filters, as the PES filter shows accelerated fouling while the PP filter retains a high percent sieving, even under the higher permeate flux of 22.5 LMH.

EXAMPLES

The following examples illustrate certain principles of the present disclosure, and are not intended to limit the scope or content of the disclosure in any way.

Example 1—Performance Comparison of Polypropylene (PP) and Polyethersulfone (PES) Filters This example provides an empirical validation of the filter performance improvements that may be achieved using PP filter elements during perfusion culture. In this example, the performance of PP filters was compared to that of PES filters.

FIGS. 2A and 2B show the permeate pressure (psi) plotted versus the process time (hours), as well as the percent sieving (%) versus the process time for the following filters: 0.2 PES (1.0 mm), 0.2 PES (0.5 mm), 0.2 PP (1.8 mm), and 0.2 PP (0.6 mm). The batch process was executed at 1.5 L working volume in a bioreactor containing Chinese hamster ovary (CHO) cells. Filter flux was set to 30 liters/$m^2 \cdot hr$. The clarification of IgG antibodies was performed under tangential flow (TF) mode. This figure shows that over time, the 0.2 PP (1.8 mm) filter produces results with a consistently high level of percent sieving and consistently low permeate pressure. Importantly, PES and PP filters having similar pore sizes behave differently in our tests: the 0.2 PES (0.5 mm) filter exhibited rapid declines in both sieving percentage and permeate pressure within the first 10 hours of the process. By contrast, the 0.2 PP (0.6 mm) filter exhibited high sieving and consistent permeate pressure for more than 20 hours, outperforming even the 1.0 mm PES filter. This indicates that the difference in material (PES vs. PP) has a significant effect on fouling performance. The use of PP filters for clarification processes may allow for extended process times and may reduce the surface area needed to clarify the same volume of culture media, potentially leading to greater yields and lower unit costs. Historically, PP filters have not been used for extended culture because it was previously assumed that PP would be denaturing for proteins. Without wishing to be bound by any theory, the results from the experiments described above suggests that these filters are not denaturing and may in fact be used over extended culture periods.

What is claimed is:

1. A filter housing comprising:
   an inlet;
   a retentate outlet;
   a permeate outlet;
   at least one pre-wetted hydrophobic hollow fiber filter extending between the inlet and the retentate outlet, thereby fluidly separating the permeate outlet from the retentate outlet and the inlet; and
   a potting material connecting the at least one hydrophobic hollow fiber filter to the filter housing and sealing at least one of the inlet and the retentate outlet from the permeate outlet,
   wherein the pre-wetted hydrophobic hollow fiber filter consists of hydrophobic polymers and lacks hydrophilic polymers, and
   wherein the filter is contained in an aqueous solution within the filter housing.

2. The filter housing of claim 1, wherein the hydrophobic hollow fiber comprises a plurality of pores.

3. The filter housing of claim 2, wherein the pores are 0.05 um to 2.0 um in diameter.

4. The filter housing of claim 1, wherein the hydrophobic hollow fiber has a surface area of 10 cm2 to 90 m2.

5. The filter housing of claim 1, wherein the hydrophobic hollow fiber has an inner diameter of 0.2 mm to 5.0 mm.

6. The filter housing of claim 1, wherein the hydrophobic hollow fiber has a wall thickness of 50 um to 500 um.

7. The filter housing of claim 1, wherein the hydrophobic hollow fiber filter comprises polypropylene, or a co-polymer thereof.

8. A method for perfusion cell culture, comprising:
   circulating a cell culture fluid through the hydrophobic hollow fiber filter in the filter housing of claim 2, thereby separating the cell culture fluid into a filtrate and a retentate; and
   returning the retentate to a bioreactor.

9. The method of claim 8, wherein the perfusion cell culture is selected from the group consisting of: n-1 culture and media exchange, in either case wherein the filtrate is not retained.

10. The method of claim 8, wherein the perfusion cell culture is selected from the group consisting of: high productivity harvest, concentrated fed batch culture, or continuous perfusion, in each case wherein the filtrate comprises a bioproduct of interest and is retained.

11. The method of claim 8, wherein the perfusion cell culture is a mammalian cell culture, yeast cell culture, prokaryotic cell culture, or insect cell culture.

12. The method of claim 8, wherein the circulation of the cell culture fluid is performed by alternating tangential flow.

13. The method of claim 8, wherein the circulation of the cell culture fluid is performed by tangential flow filtration.

14. The method of claim 8, wherein the circulation of the cell culture fluid is performed at a filter flux of 1, 2, 3, 4, 5, 10, 15, 20, 22.5, 25, 30 l/m2·h.

15. The method of claim 8, wherein the method is performed in a separation system comprising one or more of the following: peristaltic tubing through a peristaltic pumphead, maglev pump, ATF pump, and other positive displacement disposable pumps.

16. The method of claim 8, wherein the method is performed over 10, 20, 30, 40, 50 days.

17. The method of claim 8, wherein the hydrophobic hollow fiber filter comprises polypropylene or a co-polymer thereof.

18. A method of assembling a perfusion culture system comprising the filter housing of claim 1, comprising the steps of:
   disposing the pre-wetted hydrophobic hollow-fiber filter into the filter housing and, optionally, connecting a permeate outlet of the filter housing to a permeate collection vessel, wherein:
   (a) the perfusion culture system comprises a process vessel, a first conduit fluidly connecting an interior of the process vessel to an interior of the filter housing to define a filter feed channel and, optionally, a second conduit connecting the interior of the filter housing to the process vessel and defining a retentate channel, and
   (b) prior to disposal within the filter housing the hydrophobic hollow fiber filter is pre-wetted with a solution comprising an alcohol and is stored in a buffered aqueous solution.

19. The method of claim 18, wherein the filter housing further comprises an outlet for a filtrate, the outlet being fluidly separated from the filter feed and retentate channels by the hydrophobic hollow fiber filter.

20. The method of claim 18, wherein the circulation of a cell culture fluid is performed at a filter flux of 1, 2, 3, 4, 5, 10, 15, 20, 22.5, 25, 30 l/m2·h.

21. The method of claim 18, wherein the hydrophobic hollow fiber filter comprises polypropylene or a co-polymer thereof.

22. A method of perfusion cell culture, comprising:
   passing a cell culture medium through the filter housing of claim 1 and tangentially across the hydrophobic hollow fiber filter to reduce a concentration of a first component of the cell culture medium, wherein the first component does not comprise a recombinant peptide, nucleic acid or viral capsid.

23. The method of claim 22, wherein the method is performed over 10, 20, 30, 40, 50 days.

24. The method of claim 22, wherein the circulation of a cell culture fluid is performed at a filter flux of 1, 2, 3, 4, 5, 10, 15, 20, 22.5, 25, 30 l/m2·h.

25. The method of claim 22, wherein the hydrophobic hollow fiber filter comprises polypropylene or a co-polymer thereof.

26. A method of filtering a fluid, comprising:
   passing the fluid through the filter housing of claim 1 such that the fluid flows in a non-laminar manner through the hydrophobic hollow fiber filter, and such that the fluid is separated into a retentate and a permeate.

27. The method of claim 26, wherein a product of a feed velocity of the hydrophobic hollow fiber filter system and an inner diameter of the hydrophobic hollow fiber filter is greater than 2500 mm2s-1.

28. The method of claim 26, wherein a Reynolds number characterizing the flow of fluid into the hydrophobic hollow fiber filter is greater than 2000, 2300, 2500, 3000, 3500, or 4000.

29. The method of claim 26, wherein the hydrophobic hollow fiber filter comprises polypropylene or a co-polymer thereof.

30. The method of claim 26, wherein a direction of flow through the hydrophobic hollow fiber filter is alternated.

31. The method of claim 26, further comprising a step of collecting a filter permeate.

32. The method of claim 31, wherein the hydrophobic hollow fiber filter retains a non-desired species.

33. The method of claim 32, wherein the retained non-desired species is selected from the group consisting of: a species of mammalian cell origin; a species of microbial cell origin; a species of viral origin; a protein; a nucleic acid; a polysaccharide; or a complex of any of the foregoing.

34. The method of claim 31, wherein a desired species passes through the hydrophobic hollow fiber filter into a permeate.

35. The method of claim 34, wherein the desired species is selected from the group consisting of: a species of mammalian cell origin; a species of microbial cell origin; a species of viral origin; a protein; a nucleic acid; a polysaccharide; a virus; a microcarrier; a particle; or a complex of any of the foregoing.

36. A composition comprising a permeate collected according to the method of claim 35.

37. The composition of claim 36, wherein a concentration of a desired species in the composition is at least 10×, 20×, 40×, 50×, 75× or 100× greater than a concentration of the desired species in the fluid.

38. The composition of claim 36, wherein a concentration of a non-desired species is at least 10×, 20×, 40×, 50×, 75× or 100× less than a concentration of the non-desired species in the fluid.

39. A method of claim 26, further comprising the step of removing a permeate from the fluid, thereby increasing a concentration of a desired species that is retained by the hydrophobic hollow fiber filter, wherein the concentration of the desired species is increased by 5×, 10×, 20×, 40×, 50×, 75× or 100×.

40. A method of filtering a fluid, comprising:
passing the fluid through the filtration system of claim 1 under conditions in which a feed velocity through the hydrophobic hollow fiber filter is 2000, 2300, 2500, 3000, 3500 or 4000 times greater than the quotient of a kinematic viscosity of the fluid over the hollow fiber filter diameter.

* * * * *